United States Patent [19]

Imada et al.

[11] 4,223,091

[45] Sep. 16, 1980

[54] PROCESS FOR PRODUCING STEROIDAL ALCOHOLS

[75] Inventors: Yukio Imada, Yokohama; Katsuhiko Takahashi, Kawasaki, both of Japan

[73] Assignee: Mitsubishi Chemical Industries Limited, Tokyo, Japan

[21] Appl. No.: 945,349

[22] Filed: Sep. 25, 1978

[30] Foreign Application Priority Data

Oct. 14, 1977 [JP] Japan .................................. 52-123184
Oct. 14, 1977 [JP] Japan .................................. 52-123185

[51] Int. Cl.² ........................................... C12P 33/16
[52] U.S. Cl. ...................................... 435/55; 435/863
[58] Field of Search ........................ 195/51 G; 435/55

[56] References Cited

U.S. PATENT DOCUMENTS

| | | | |
|---|---|---|---|
| 3,677,920 | 7/1972 | Kai | 260/859 R |
| 3,678,014 | 7/1972 | Suzuki | 260/859 R |
| 3,684,657 | 8/1972 | Kraychy et al. | 195/51 G |
| 3,759,791 | 9/1973 | Marsheck et al. | 195/51 G |
| 3,873,640 | 3/1975 | Owston | 260/859 R |
| 4,018,851 | 4/1977 | Baccei | 260/859 R |

*Primary Examiner*—Alvin E. Tanenholtz
*Attorney, Agent, or Firm*—Oblon, Fisher, Spivak, McClelland & Maier

[57] ABSTRACT

Steroidal alcohols are produced by cultivating a microorganism belonging to the genus Mycobacterium and capable of producing 20 α-hydroxymethylpregna-1,4-dien-3-one or 20 α-hydroxymethylpregn-4-en-3-one as a main product in the 859 R

9 Claims, No Drawings

PROCESS FOR PRODUCING STEROIDAL ALCOHOLS

BACKGROUND OF THE INVENTION

1. Field of the Invention

This invention relates to a process for producing steroidal alcohols, and more particularly to the microbiological oxidation of a sterol to 20α-hydroxymethylpregna-1,4-dien-3-one and/or 20α-hydroxymethylpregn-4-en-3-one with a new microorganism.

2. Description of the Prior Art

20α-Hydroxymethylpregna-1,4-dien-3-one (22-hydroxy-23, 24-bisnorchola-1,4-dien-3-one) (hereinafter referred to as HPD) and 20α-hydroxymethylpregn-4-en-3-one (22-hydroxy-23, 24-bisnorchola-4-en-3-one) (hereinafter referred to as 4HP) are significant intermediates for the synthesis of valuable steroids such as corticosteroids, progestogens, anabolic hormones and the like.

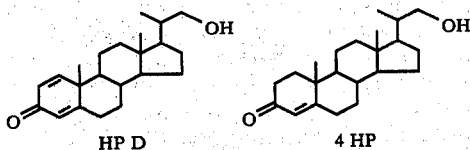

HP D          4 HP

It has been known that HPD and 4HP are formed by cultivating microorganisms belonging to the genus Mycobacterium (See (A) Applied Microbiology 23 No. 1 72–77 (1972); (B) U.S. Pat. No. 3,684,657; and (C) U.S. Pat. No. 3,759,791). However, in the processes described in the above literatures, only slight amounts of HPD and 4HP are formed, and therefore, the above processes are commercially insignificant. That is to say, the concentrations of HPD formed in the processes described in literatures A, B and C are reported to be about 20, 40 and lower than 20 μg per ml of the culture medium, respectively.

It is also described in an example of literature C that 4HP is formed at a concentration of only 40 μg/ml. However, the main product in the above processes is androsta-1,4-diene-3,17-dione (hereinafter referred to as ADD) or androst-4-ene-3,17-dione (hereinafter referred to as 4AD), and the ratio of the formed HPD and 4HP to the main product is less than 1/10.

Therefore, there is a continuing need for developing a commercially attractive process for producing HPD and 4HP.

SUMMARY OF THE INVENTION

It has now been discovered that HPD and 4HP are obtained at high yields and concentrations, by the microbiological oxidation of a sterol, its C-3 ester derivative, its C-3 -ether derivative or an intermediate in the oxidation thereof with a microorganism belonging to the genus Mycobacterium and capable of producing HPD or 4HP as the main product.

DESCRIPTION OF THE PREFERRED EMBODIMENTS

As stated above, this invention is directed to the microbiological oxidation of a sterol to HPD and/or 4HP.

The microorganism which can be used in the process of this invention belongs to the genus Mycobacterium and is capable of producing HPD or 4HP as the main product. It goes without saying that any microorganism can be used, so long as it produces HPD, 4HP or a mixture thereof as the main product. As contemplated in the specification as well as in the claims, to produce HPD or 4HP as the main product means a molar percent yield of HPD plus 4HP for the consumed sterol substrate exceeding 50%. That is to say, the following equation exists:

$$Y = g_1/(G + g_2/G) \times 100 > 50$$

wherein Y represents percent yield, $g_1$ amount of formed HPD (mole), $g_2$ amount of formed 4HP (mole), and G amount of consumed sterol (mole).

Known microorganisms belonging to the genus Mycobacterium (hereinafter referred to as wild strains) do not produce HPD or 4HP as the main product, even if fermentation is effected using a sterol as a substrate. Therefore, the microorganisms used in the process of this invention can be clearly distinguished from the wild strains in that the microorganisms of this invention produce HPD or 4HP as the main product. Such microorganisms include mutants which are lacking in or weak in the enzymes degrading HPD and/or 4HP or the enzyme active at a later stage of the metabolic pathway. Moreover, among such microorganisms are included mutants which are lacking in or weak in the enzymes active somewhere in the metabolic pathway from a sterol to 4AD or ADD (for example, 23, 24-bisnorchola-1,4-dienecarboxylic acid) thereby shifting the main metabolic pathway to HPD and/or 4HP to accumulate HPD and/or 4HP.

An example of such mutants is *Mycobacterium parafortuitum* complex MCI 0617 which is obtained by treating parent strain *Mycobacterium parafortuitum* complex ATCC 25790 (*Mycobacterium neoaurum* ATCC 25790) with ultraviolet light. This mutant has been given the accession number FERM-P-4258 by the Fermentation Research Institute, Agency of Industrial Science and Technology, where it has been deposited, MCI 0617 has also been given the accession number NRRL B-11389 by the Northern Regional Research Center of the U.S. Department of Agriculture in whose culture collection the microorganism has been deposited.

According to the second co-operative study by the international Working Group on Mycobacterial Taxonomy (IWGMT), ATCC 25790, i.e., the parent strain of the present mutant, was referred to as the "*Mycobacterium parafortuitum* complex" (H. Haito et al. 1977. Int. J. Syst. Bacteriol., 27, 75–85).

*Mycobacterium aurum*, newly proposed by M. Tsukamura (the type strain is Tsukamura #358 (ATCC 23366)), included originally Tsukamura #309 (ATCC 25790). (M. Tsukamura, 1966. Med. Biol. (Tokyo), 72, 270–273). Subsequently, Tsukamura described *Mycobacterium neoaurum* as a new species (the type strain is Tsukamura #3503; ATCC 25795) distinguishing from *M. aurum*. However, ATCC 25790 was retained in *M. aurum* (M. Tsukamura. 1972. Med. Biol. (Tokyo), 85, 229–233).

In the second co-operative IWGMT study, they (H. Saito et al., l.c., p. 77, FIG. 1) suggested, however, that ATCC 25790 was included in Cluster 8 (referable to *M. neoaurum*, not *M. aurum*) having 90% internal similarity, containing eight strains, and including ATCC 25795, the type strain of *M. neoaurum*. Additionally Saito et al. (l.c.) concluded that "there appears to be considerable intertaxon similarity in the one complex which contained *M. parafortuitum* (Tsukamura), *M. diernhoferi* (B'uml/o/ nicke et Juhasz), *M. aurum* (Tsukamura), *M. neoaurum* (Tsukamura), and a cluster of Kanazawa strains. It is felt that such closely related, normally saprophytic, rapidly growing mycobacteria should not be segregated, but rather understood to be a complex, designated the "*M. parafortuitum* complex," until such time as more definitive identification is possible."

M. Tsukamura and S. Mizuno (1977. J. Gen. Microbiol., 98, 511–517) also came to the similar conclusion that *M. parafortuitum*, *M. aurum*, and *M. neoaurum* are regarded to be three subspecies of the species *M. parafortuitum* or a complex, i.e., the "*M. parafortuitum* complex."

The morphological and physiological characteristics of the *M. parafortuitum* complex and a comparison with its related taxa have been summarized in the tables of the following papers: H. Saito. 1975. Kekkaku, 50, 402, Table; H. Saito et al. 1977, l.c., 80–81, Table 2; and M. Tsukamura and S. Mizuno. 1977. l.c., 515, Table 3.

As stated above, it seems to be reasonable that the taxonomic position of the parent strain ATCC 25790 (Tsukamura #309) is determined as the *M. parafortuitum* complex, based on the second cooperative TWGMT study.

The characters of the *M. parafortuitum* complex are: Gram-positive; acid-fast; non-motile; non-spore-forming; occurs as rods; rapid-growth; scotochromogenic; refers to the Runyon's Group IV. The mutant MCI-0617, derived from the parent strain ATCC 25790, hardly differs from the parent strain in taxonomical property, except that the former formed rough colonies on agar media. Therefore, Strain MIC-0617 is referable to the *M. parafortuitum* complex because the parent strain, as mentioned above, is assigned to the *M. parafortuitum* complex.

It is apparent that the present new mutant differs from both Strains Mycobacterium sp. NRRL B-3683 and NRRL B-3805 (recently, NRRL B-3805 was identified and mentioned as *Mycobacterium vaccae* in Japanese Patent Application Publication (KOKAI) No. 105,289/1977) which were disclosed as the 4AD- and ADD-producing mutant strains in U.S. Pat. Nos. 3,759,791 and 3,684,657.

With respect to the comparison between these taxa, see the following references; R. E. Buchanan and N. E. Gibbons (co-eds.). 1974. "Bergey's Manual of Determinative Bacteriology, ed. 8," pp. 659–696, Williams and Wilkins Co., Baltimore; H. Saito. 1975. Kekkaku, 50, 402; H. Saito et al. 1977. Int. J. Syst. Bacteriol., 27, 80–81; and, M Tsukamura and S. Mizuno. 1977. J. Gen. Microbiol., 98, 515. Strain MCI-0617 differs from both Strains NRRL B-3805 and MRRL B-3683 taxonomically and also phyiologically (i.e., in the degradation of ADD, 4D, and 9α-OH-4AD); viz., the former grows poorly on these substrates, while the latter does not grow.

As mentioned above, the mutant MCI-0617, derived from the parent strain ATCC 25790, is referable to the *M. parafortuitum* complex, and additionally, it is clear distinguished taxonomically from all known mutant strains producing ADD and 4AD.

The steroid substrates for the process of this invention include sterols, their C-3 ester derivatives, their C-3 ether derivatives and their intermediates in the oxidation thereof.

Sterols possess a hydroxy group at C-3, normally a double bond at C-5, a side chain of 8 to 10 carbon atoms at C-17, and in some cases, a double bond at C-7, C-8, C-9 (11) or the like of the perhydrocyclopentanophenanthrene nucleus. Examples of such sterols are cholesterol, stigmasterol, campesterol, sitosterol, ergosterol, brassicasterol, fucosterol, lanosterol, agnosterol, dihydrolanosterol and dihydroagnosterol. Especially preferred are cholesterol, campesterol and sitosterol.

C-3 ester derivatives of 3β-OH of sterols, and inorganic acids, e.g., sulfuric acid, or organic acids, e.g., fatty acids, can also be used as the starting material for the process of this invention.

Examples of such C-3 ester derivatives are cholesteryl oleate, cholesteryl palmitate and cholesteryl sulfate.

Further, C-3 ether derivatives which are obtained, for example, by the addition of alkylene oxide to 3β-OH of sterols can be used as the starting material for the process of this invention.

An example of such C-3 ether derivatives is polyoxyethylene cholesteryl ether.

It goes without saying that wool wax and lanolin each containing the above-described C-3 ester derivatives of the sterols; cholesterol-containing wool alcohol which is obtained by the hydrolysis of lanolin; and a C-3 ether derivative polyoxyethylene lanolin alcohol ether which is obtained by the reaction of wool alcohol with ethylene oxide can be used as the starting materials for the process of this invention.

Sterols-containing natural products and processed materials, such as waste oil obtained in purifying fish oil or cuttlefish oil by washing it with alkali, deodorized scum and sludge of vegetable oils, and tall oil can also be used as the starting materials for the process of this invention.

Intermediates in the oxidation of sterols, their C-3 ester derivatives or their C-3 ether derivatives can be used as the starting materials for the process of this invention. The oxidation intermediates include 4-en-3-one derivatives and 1,4-dien-3-one derivatives of sterols such as, for example, cholest-4-en-3-one, cholesta-1,4-dien-3-one and cholesta-4,22-dien-3-one.

In a preferred embodiment of this invention, a medium containing at least 0.1 percent by weight of glycerides is used.

The glycerides which are added to the culture medium include monoglycerides, diglycerides and triglycerides.

Likewise, single glycerides containing identical fatty acid residues, and mixed glycerides containing two or three different fatty acid residues can also be employed. The fatty acid residues include unsaturated fatty acid residues and saturated fatty acid residues.

From the hydrophilic viewpoint, it is preferred that the fatty acid residue contain up to 26 carbon atoms.

Examples of suitable single glycerides are monoglycerides such as α-monoacetin, β-monoacetin, α-monopalmitin, β-monopalmitin, α-monostearin, β-monostearin, α-monoolein, β-monoolein and the like; diglycerides such as α,α'-diacetin, α,β-diacetin, α,α'-dipalmitin, α,β-dipalmitin, α,α'-distearin, α,β-distearin, α,α'-diolein, α,β-diolein and the like; and triglycerides such as triacetin, trilaurin, trimyristin, tripalmitin, tristearin, triolein and the like.

Examples of suitable mixed glycerides are 1-aceto-2,3-dipalmitin, 1-palmito-2,3-dicaprin, 1-lauro-2-milisto-3-palmitin, 2-oleo-1,3-dipalmitin and 2-stearo-1,3diolein. In the process of this invention, fats can be used in place of the glycerides.

As used hereinabove, and as will be used hereinafter and in the claims, the term "fats" is intended to include vegetable fats and oils, and animal fats and oils rgardless of their physical state.

Examples of suitable fats of plant origin are linseed oil, perilla oil, tung oil, sesame oil, corn oil, rapeseed oil, cottonseed oil, safflower oil, soybean oil, soya lecithin, camellia oil, rice bran oil, olive oil, castor oil, peanut oil, coconut oil, palm oil and palm kernel oil. Examples of suitable fats of animal origin are fish oil, whale oil, beef tallow, lard, mutton tallow, beef foot oil and liver oil.

It is not necessary to purify the above-listed naturally occurring fats to a sufficient degree. However, it is preferred to remove in advance substances which are detrimental to the microbiological oxidation.

Examples of preferred fats of plant origin are edible fats such as olive oil, soybean oil, soya lecithin, cottonseed oil, corn oil, sesame oil, rapeseed oil, peanut oil, camellia oil, palm oil, coconut oil and the like. Cottonseed oil, soybean oil, rapeseed oil and palm oil are especially preferred due to their stable supply. Examples of preferred fats of animal origin are lard and tallow oil.

A glyceride-containing substance can be used alone or if desired a mixture of two or more glyceride-containing substances of the same sort or different sorts can also be used.

The use of a small amount of glyceride-containing substances increases the yields of HPD and/or 4HP only to a slight extent. On the other hand, the use of an excess of glyceride-containing substances is not preferred, since it causes inhibition and the glyceride-containing substances become massive. Therefore, the glyceride-containing substances are added to the culture medium to give normally about 0.1 to 10 percent by weight, preferably about 0.2 to 7 percent by weight and more preferably about 0.3 to 4 percent by weight of glycerides in the culture medium.

Oil seeds and oil fruits can be added to the culture medium to give a concentration of glycerides in the above-described range.

Examples of suitable oil seeds and oil fruits are linseed, soybean, rapeseed, cottonseed, sesame, peanut, safflower, corn and rice bran.

The addition of vegetable oil meals along with the glyceride-containing substance to the culture medium has a beneficial effect on the production of HPD and/or 4HP and increases the yields of HPD and/or 4HP.

As used hereinabove, and as will be used hereinafter and in the claims, the term "vegetable oil meals" is intended to include refuses of vegetable fats and oils, which are the crushed residue from the extraction of oil-bearing seeds or fruits. Depending upon the extractive process, varying percentages of protein and fats will remain in the meals. However, any vegetable oil meals may be employed.

In general, commercially available vegetable oil meals are preferred.

Examples of suitable vegetable oil meals are soybean oil meal, linseed oil meal, perilla oil meal, rapeseed oil meal, cottonseed oil meal, sesame oil meal, peanut oil meal, safflower oil meal, tung oil meal, defatted corn powder, camellia oil meal, defatted rice bran, olive oil meal, coconut oil meal and palm oil meal.

It is preferred that vegetable oil meals be ground to a degree of fineness such that they are well assimilated by the microorganism.

A vegetable oil meal can be used alone or in combination with other vegetable oil meals.

The use of a small amount of vegetable oil meals increases the yields of HPD and/or 4HP only to a slight extent. On the other hand, the use of an excess of vegetable oil meals increases the viscosity of the fermentation broth and makes difficult the stirring. Therefore, the vegetable oil meals are added to the culture medium to give a concentration of normally about 0.5 to 20 percent by weight, preferably about 1 to 15 percent by weight and more preferably about 1.5 to 10 percent by weight.

In addition to the glyceride-containing substance and the vegetable oil meal, carbon sources, nitrogen sources and inorganic substances are incorporated in the culture medium.

Examples of such carbon sources are hydrocarbon; alcohols such as methanol, ethanol; organic acids such as succinic acid, acetic acid, and the like, and the salts thereof; and saccharides such as starch, maltose, sucrose, glucose, rhamnose and the like.

Natural nutrient sources containing carbon sources, nitrogen sources and other nutrient substances may be incorporated in the culture medium.

Examples of such natural nutrient sources are molasses including hightest molasses and xylose molasses; bagasse, corn cob, alfalfa, corn steep liquor, distillers' solubles, mieki (an aqueous solution of amino acids mixture prepared by the hydrolysis of soybean oil meal with HCl), fish meal, yeast, bran, meat extract, yeast extract, potato extract, malt extract, gluten, peptone, glutamates, asparagine, glycine, casein, casein hydrolysate and skimmed milk.

Examples of the suitable inorganic substances which are incorporated in the culture medium are nitrogen sources such as ammonium sulfate, ammonium chloride and the like; potassium and phosphorus sources such as dipotassium hydrogenphosphate; salts of iron, copper, magnesium, manganese, cobalt, zinc, calcium and the like; and ashes of natural products such as molasses.

Other components, e.g., vitamins, can be present in the culture medium if they do not impede the function of the main components.

The compostion of the culture medium depends on the microorganism which is used. Carbon sources, nitrogen sources, potassium, phosphorus and magnesium are critical as components in the culture medium.

An anti-foaming agent, e.g., polyoxyalkylene glycol, may be incorporated in the culture medium, if necessary. However, it need not always be added.

The culture medium can contain a surface active agent. This is not required, but does normally render the culture medium more conducive to manipulation.

Examples of the suitable surface active agents are nonionic and anion surface active agents such as polyoxyethylene sorbitan monostearate, sorbitan monopalmitate and polyethylene glycol monostearate.

In general, the incubation temperature is in the range of 20° to 40° C. The preferred incubation temperature is about in the range of 30° to 35° C.

The pH of the culture medium is adjusted to normally 5 to 10 and preferably 6 to 9. Because a microorganism which is used in the process of this invention belongs to the genus Mycobacterium, it can stand at a pH of about 10 as is well known in the art.

In general, the steroid substrate is sterilized with the culture medium. It can also be added to the culture medium after the start of incubation. In addition, it can be added in portions.

The sterol substrate, after sterilization by dry heat or wet heat, is added in any suitable manner, such as in the form of a powder or a solution in a suitable solvent, e.g., dimethylformamide, or in the form of a suspension prepared by ultrasonically dispersing it.

It is preferred that the sterol substrate and the surface active agent be simultaneously added because of the increased emulsification of the sterol substrate.

The incubation time is not critical. In general, the amount of the formed HPD and/or 4HP increases rapidly three days after the addition of the sterol substrate. Thereafter, the amount of the formed HPD and/or 4HP increases gradually with the incubation time. However, the incubation time of not less than 20 days is of little commercial value.

Upon completion of the fermentation, the resulting HPD and/or 4HP is recovered from the fermentation broth by conventional methods. For example, crude HPD and/or 4HP is obtained by extracting HPD and/or 4HP with several times as much a water-immiscible organic solvent, e.g., ethyl acetate, as HPD plus 4HP, and then removing the solvent from the extract. If the separation of HPD, 4HP, the sterol substrate and the by-products is required, they can be separated by column chromatography using silica gel, alumina or porous resins as adsorbent, and petroleum ether, benzene, chloroform, ether, acetone, methanol, ethyl acetate or the like as eluent. The separated HPD or 4HP may be further purified by repeatedly recrystallizing it from a suitable solvent, e.g., 10% ethanol-hexane.

In accordance with the process of this invention, HPD and/or 4HP can be obtained at a yield of not less than 50 mole % and generally not less than 70 mole % based on the consumed sterol.

In addition, the process of this invention is commercially advantageous in that the incubation at a high concentration of the substrate (e.g., 1–4%) increase the yield of HPD and/or 4HP.

Having generally described this invention, a more complete understanding can be obtained by reference to certain examples which are provided herein for purposes of illustration only are not intended to be limiting in any manner.

In the following examples, analysis of sterols, their derivatives, HPD, 4HP, remaining sterols and by-products steroids is made by gas chromatography. Unless otherwise stated, the percentages in the following examples are by weight.

EXAMPLE 1

A seed medium (pH 7.2) having the following composition is prepared:
 1.0 percent of glucose
 1.0 percent of meat extract
 1.0 percent of peptone, and
 remainder—water To a 500 ml shaker flask is added 100 ml of the seed medium. The flask and its contents are sterilized by autoclaving for a period of 15 minutes at a temperature of 120° C. The medium is inoculated with a loopful of *Mycobacterium parafortuitum* complex MCI 0617 and the inoculated medium is incubated for a period of 72 hours at a temperature of 30° C. on a reciprocal shaker having a 7-cm stroke at 120 strokes per minute.

To each of ten (10) 500 ml shaker flasks is added 50 ml of a main fermentation medium (pH 7.0) having the following composition:
 4 percent of soybean oil meal
 0.2 percent of $K_2HPO_4$
 0.1 percent of $MgSO_4.7H_2O$
 2 percent of fish oil residue
 0.2 percent of $NaNO_3$
 1.0 percent of cholesterol The flasks and their contents are sterilized by autoclaving for a period of 20 minutes at a temperature of 120° C. Each of the flask is inoculated with 2 ml of the seed culture broth obtained above. The main fermentation is initiated at a temperature of 30° C. on a reciprocal shaker having a 7-cm stroke at 120 strokes per minute. At the end of 160 hours from the time of initiating the incubation, the incubation is stopped. The combined fermentation broth is extracted twice with 2 l of ethyl acetate. Upon filtration of insoluble materials of the combined extract, such as cells, analysis shows the content of the steroids in the extract as follows: the remaining substrate cholesterol 0.05 g, HPD 2.65 g and 4HP 0.22 g.

It follows that HPD and 4HP are produced at a yield of about 85% for the consumed sterol. The by-products contain 0.03 g of ADD. The extract is chromatographed on silica gel, and eluted with 20% ethyl acetate-n-hexane, thereby separating HPD and 4HP, further the remaining substrate and by-products. Each of the HPD and 4HP fractions eluted is concentrated and then purified by evaporating the solvent and then recrystallizing it twice from 10% ethanol-heptane to give pure crystals of 2.45 g of HPD and 0.17 g of 4HP.

They are identical in melting point, mass spectrometry, NMR and IR with those described in the literatures.

EXAMPLE 2

Example 1 is repeated except that various sterols indicated in Table 1 are used as starting sterols in place of cholesterol.

TABLE 1

|  | Product (g) | | Remaining substrate |
|---|---|---|---|
|  | HPD | 4HP |  |
| β-Sitosterol + Campesterol (2:1 mixture) | 1.88 | 0.12 | 0.67 |
| Cholest-4-en-3-one | 1.33 | 0.08 | 1.48 |
| Cholesta-1,4-dien-3-one | 2.13 | 0.02 | 0.85 |
| Cholesteryl oleate | 0.29 | 0.03 | 3.10 |

EXAMPLE 3

Example 1 is repeated except that a main aqueous fermentation medium having the following composition is used:
 6 percent of ground soybean,
 0.25 percent of $K_2HPO_4$,
 1 percent of yeast
 0.1% of $MgSO_4.7H_2O$
 a concentration of cholesterol indicated in Table 2

The results are shown in Table 2.

Table 2

| Concentration of Cholesterol (weight %) | HPD (g) | 4HP (g) | Remaining Cholesterol (g) |
|---|---|---|---|
| 0.2 | 0.68 | 0.06 | 0.0 |
| 0.5 | 1.35 | 0.10 | 0.0 |

Table 2-continued

| Concentration of Cholesterol (weight %) | HPD (g) | 4HP (g) | Remaining Cholesterol (g) |
|---|---|---|---|
| 0.8 | 2.57 | 0.13 | 0.15 |
| 1.0 | 2.81 | 0.18 | 0.40 |

EXAMPLE 4

Example 1 is repeated except that a 5 l shaker flask containing 800 ml of a culture medium containing 1.0% of glucose, 1.0% of meat extract, 1.0% of peptone, 0.5% of Tween-80 (trademark of Kao Atlas Co., Ltd. for a surface active agent), 1.0% of cholesterol and the remainder-water; and that the main fermentation is carried out at 30° C. on a reciprocal shaker having a 7-cm stroke at 100 strokes (per minute for 150 hours after the flask is inoculated with 20 ml of the seed culture broth. Analysis of the ethyl acetate extract shows the presence of 0.90 g of HPD and 0.76 g of 4HP. The amount of cholesterol which remains unreacted is 4.8 g.

EXAMPLE 5

A seed medium (pH 7.2) having the following composition is prepared:
 1.0 percent of glucose
 1.0 percent of meat extract
 1.0 percent of peptone, and
 remainder—water To a 500 ml shaker flask is added 100 ml of the seed medium. The flask and its contents are sterilized by autoclaving for a period of 15 minutes at a temperature of 120° C. The medium is incoculated with a loopful of *Mycobacterium parafortuitum complex* MCI 0617 and the inoculated medium is incubated for a period of 72 hours at a temperature of 30° C. on a reciprocal shaker having a 7-cm stroke at 120 strokes per minute.

To each of ten (10) 500 ml shaker flask is added 50 ml of a main fermentation medium (pH 7.0) having the following composition:
 5.0 percent of soybean oil meal,
 0.2 percent of $K_2HPO_4$,
 0.1 percent of $MgSO_4.7H_2O$,
 1.0 percent of cottonseed oil
 0.2 percent of $NaNO_3$
 0.8% of cholesterol, and
 remainder—water The flasks and their contents are sterilized by autoclaving for a period of 20 minutes at a temperature of 120° C. Each of the flasks is inoculated with 2 ml of the seed culture broth obtained above. The main fermentation is initiated at a temperature of 30° C. on a reciprocal shaker having a 7-cm stroke at 120 strokes per minute. At the end of 150 hours from the time of initiating the incubation, the incubation is stopped. The combined fermentation broth is extracted twice with 2 l of ethyl acetate. Upon filtration of insoluble matters such as cells, the content of HPD and 4HP in the extract is analyzed by gas chromatography. The results are shown in Table 3. The extract is chromatographed on silica gel, and eluted with 20% ethyl acetate-n-hexane, thereby separating the HPD and 4HP formed, further the substrate cholesterol and the by-products. HPD and 4HP can be purified by recrystallizing the HPD and 4HP fractions from 10% ethanol-heptane.

Employing a mixture of β-sitosterol and campesterol (2:1), cholest-4-en-3-one, cholesta-1,4-dien-3-one or cholesteryl oleate in place of cholesterol, the above incubation is repeated.

Likewise, the results are shown in Table 3. For comparison, the results which are obtained when the cottonseed oil is not added are shown together.

The cottonseed oil used is a mixture of nearly 100% of glycerides. The same is true for the oils used in the following examples.

TABLE 3

| Substrate | Added Substrate | Product (g) HPD | 4HP | Remaining Substrate (g) |
|---|---|---|---|---|
|  | None | 0.62 | 0.04 | 2.68 |
| Cholesterol | Cottonseed Oil | 2.36 | 0.14 | 0.13 |
| Sitosterol + | None | 0.43 | 0.03 | 3.12 |
| Campesterol | Cottonseed Oil | 1.63 | 0.08 | 0.45 |
| Cholest-4-en-3-one | None | 0.44 | 0.02 | 3.25 |
|  | Cottonseed Oil | 1.16 | 0.08 | 2.05 |
| Cholesta-1,4-dien-3-one | None | 0.57 | 0.01 | 3.05 |
|  | Cottonseed Oil | 1.89 | 0.03 | 0.65 |
| Cholesteryl Oleate | None | 0.11 | 0.01 | 3.65 |
|  | Cottonseed Oil | 0.28 | 0.03 | 3.20 |

EXAMPLE 6

Example 5 is repeated except that various glycerides and oils are added to the main fermentation medium in place of cottonseed oil. The results are shown in Table 4.

TABLE 4

| Oil | Yield of HPD (g) | Yield of 4HP (g) |
|---|---|---|
| None | 0.62 | 0.04 |
| Olive oil | 2.15 | 0.13 |
| Corn oil | 2.20 | 0.17 |
| Rice bran oil | 2.18 | 0.13 |
| Palm oil | 2.45 | 0.19 |
| Coconut oil | 2.35 | 0.13 |
| Soybean oil | 2.36 | 0.14 |
| Sesame oil | 2.15 | 0.12 |
| Peanut oil | 2.09 | 0.12 |
| Linseed oil | 2.09 | 0.12 |
| Sardine oil | 2.50 | 0.21 |
| Lard | 2.20 | 0.12 |
| Triolein | 2.09 | 0.12 |
| Tripalmitin | 2.33 | 0.13 |
| α-Monostearin | 1.72 | 0.10 |
| α,α'-Distearin | 1.75 | 0.10 |

EXAMPLE 7

Example 5 is repeated except that various concentrations of tristearin are used in place of 1% of cottonseed oil. The results are shown in Table 5.

TABLE 5

| Concentration of Tristearin (weight %) | Product HPD (g) | 4HP (g) |
|---|---|---|
| 0 | 0.55 | 0.04 |
| 0.10 | 0.98 | 0.07 |
| 0.2 | 1.15 | 0.07 |
| 0.3 | 1.43 | 0.08 |
| 0.5 | 1.75 | 0.10 |
| 1.0 | 2.40 | 0.15 |
| 1.5 | 2.61 | 0.15 |
| 2.0 | 2.55 | 0.16 |
| 3.0 | 1.55 | 0.08 |
| 4.0 | 1.21 | 0.07 |
| 7.0 | 0.80 | 0.05 |
| 10.0 | 0.70 | 0.05 |

EXAMPLE 8

Example 5 is repeated except that a main fermentation medium having the following composition is used:
2 percent of glucose,
0.15 percent of $K_2HPO_4$,
1.0 percent of palm oil,
0.2 percent of $(NH_4)_2SO_4$
0.1 percent of $MgSO_4.7H_2O$
1.0 percent of yeast
4 percent of a vegetable oil meal, and
remainder—water
The results are shown in Table 6.

TABLE 6

| Vegetable Oil Meal | Product (g) | |
|---|---|---|
| | HPD | 4HP |
| None | 0.42 | 0.07 |
| Cottonseed oil meal | 2.17 | 0.12 |
| Soybean oil meal | 2.25 | 0.20 |
| Rapeseed oil meal | 1.60 | 0.13 |
| Sesame oil meal | 2.01 | 0.21 |
| Safflower oil meal | 0.95 | 0.11 |

EXAMPLE 9

Example 5 is repeated except that a main fermentation medium having the following composition is used:
2.0 percent of fish oil residue,
0.2 percent of $K_2HPO_4$,
0.1 percent of $MgSO_4.7H_2O$,
0.2 percent of $NaNO_3$
0.8 percent of cholesterol
6.0 percent of ground soybean (about 17% glyceride content), and
remainder—water The above procedure is repeated except that 3.0% of ground peanut (about 35% glyceride content), 2.5% of ground rapeseed (about 40% glyceride content) or 2.5% of ground sesame (about 40% glyceride content) is used in place of ground soybean.

The results are shown in Table 7.

TABLE 7

| Oil Seed . Oil Fruit | Product (g) | |
|---|---|---|
| | HPD | 4HP |
| None | 0.82 | 0.09 |
| Soybean | 2.67 | 0.25 |
| Peanut | 2.48 | 0.20 |
| Rapeseed | 2.02 | 0.20 |
| Sesame | 1.89 | 0.18 |

Having now fully described the invention, it will be apparent to one of ordinary skill in the art that many changes and modifications can be made thereto without departing from the spirit or scope of the invention as set forth herein.

What is claimed as new and intended to be secured by Letters Patent of the United States is:

1. A process for producing 20 α-hydroxymethyl-pregna-1,4-diene-3 one, 20 α-hydroxymethyl-pregna-4-en-3-one, or mixtures thereof, which comprises cultivating a microorganism which is a mutant belonging to the *Mycobacterium parafortuitum* complex and being capable of producing 20α-hydroxymethyl-pregna-1,4-diene-3-one or 20α-hydroxymethylpregna-4-en-3-one from a sterol in the presence of a sterol substrate.

2. A process according to claim 1 wherein said sterol substrate is selected from the group consisting of sterols, their C-3 ester derivatives, their C-3 ether derivatives and the intermediates in the oxidation thereof.

3. A process according to claim 1 wherein the microorganism belongs to *Mycobacterium neoaurum*.

4. A process according to claim 1 wherein the microorganism is *Mycobacterium parafortuitum* complex NRRL B-11389.

5. A process according to claim 1 wherein the microorganism is lacking in or weak in the enzymes degrading 20α-hydroxymethylpregna-1,4-dien-3-one or 20α-hydroxymethylpregn-4-en-3-one.

6. A process according to claim 1 wherein the cultivation is effected in the culture medium containing at least one glyceride and having a glyceride concentration of at least 0.1 percent by weight.

7. A process according to claim 1 wherein the cultivation is effected in the culture medium containing at least one glyceride and at least one vegetable oil meal, and having a glyceride concentration of at least 0.1 percent by weight.

8. The process according to claim 6, wherein the pH of the culture medium is from 5 to 10 and the incubation temperature is in the range of from 20° C. to 40° C.

9. The process according to claim 6, wherein the pH of the culture medium is from 6 to 9 and the incubation temperature is in the range of from 30° C. to 35° C.

* * * * *